United States Patent [19]

Ansher-Jackson et al.

[11] Patent Number: 5,100,657
[45] Date of Patent: Mar. 31, 1992

[54] CLEAN CONDITIONING COMPOSITIONS FOR HAIR

[75] Inventors: Phyllis M. Ansher-Jackson; Sue A. Etter, both of Cincinnati; Kathleen B. Jividen, Lebanon; Patrick C. McCall; Drew D. Setser, both of Cincinnati, all of Ohio

[73] Assignee: The Procter & Gamble Company, Cincinnati, Ohio

[21] Appl. No.: 517,290

[22] Filed: May 1, 1990

[51] Int. Cl.$^5$ .............................................. A61K 7/08
[52] U.S. Cl. ................................................. 424/70
[58] Field of Search ............... 424/70, 78, 71, DIG. 1

[56] References Cited

U.S. PATENT DOCUMENTS

| | | | |
|---|---|---|---|
| 2,643,375 | 6/1953 | Gant | 132/7 |
| 3,155,591 | 11/1964 | Hilfer | 167/87 |
| 3,325,439 | 6/1967 | Steinbach | 260/32.8 |
| 3,341,465 | 9/1967 | Kaufman et al. | 252/316 |
| 3,395,041 | 7/1968 | Hsiung | 132/7 |
| 3,579,632 | 5/1971 | Sonnen | 424/70 |
| 3,580,853 | 5/1971 | Parran | 252/152 |
| 3,681,122 | 8/1972 | Domicone et al. | 117/124 |
| 3,723,325 | 3/1973 | Parran | 252/106 |
| 3,929,678 | 12/1975 | Laughlin et al. | 252/526 |
| 3,957,970 | 5/1976 | Korkis | 424/70 |
| 3,959,461 | 5/1976 | Bailey et al. | 424/70 |
| 3,964,500 | 6/1976 | Drakoff | 132/7 |
| 4,165,369 | 8/1979 | Watanabe | 424/70 |
| 4,185,087 | 1/1980 | Morlino | 424/70 |
| 4,221,688 | 9/1980 | Johnson et al. | 260/29.2 |
| 4,228,277 | 10/1980 | Landoll | 536/90 |
| 4,243,802 | 1/1981 | Landoll | 536/91 |
| 4,269,824 | 5/1981 | Villamarin et al. | 424/70 |
| 4,275,055 | 6/1981 | Nachtigal et al. | 424/70 |
| 4,298,728 | 11/1981 | Majewicz et al. | 536/96 |
| 4,299,817 | 11/1981 | Hannan, III et al. | 424/70 |
| 4,331,167 | 5/1982 | Wajaroff | 132/7 |
| 4,336,246 | 6/1982 | Leon-Pekarek | 424/70 |
| 4,344,763 | 8/1982 | Tolgyesi et al. | 8/127.51 |
| 4,352,916 | 10/1982 | Landoll | 526/200 |
| 4,364,837 | 12/1982 | Pader | 252/173 |
| 4,374,825 | 2/1983 | Bolich, Jr. et al. | 424/70 |
| 4,387,090 | 6/1983 | Bolich, Jr. | 424/70 |
| 4,415,701 | 11/1983 | Bauer | 524/612 |
| 4,421,740 | 12/1983 | Burton | 424/70 |
| 4,426,485 | 1/1984 | Hoy et al. | 524/591 |
| 4,435,217 | 3/1984 | House | 106/171 |
| 4,450,152 | 5/1984 | Ona et al. | 424/70 |
| 4,458,068 | 7/1984 | Warner et al. | 536/91 |
| 4,459,285 | 7/1984 | Grollier et al. | 424/74 |
| 4,465,517 | 8/1984 | Shields | 106/35 |
| 4,472,375 | 9/1984 | Bolich, Jr. et al. | 424/70 |
| 4,485,089 | 11/1984 | Leipold | 424/49 |
| 4,487,883 | 12/1984 | Homan | 524/792 |
| 4,496,708 | 1/1985 | Dehm et al. | 528/76 |
| 4,501,617 | 2/1985 | Desmarais | 106/93 |
| 4,502,889 | 3/1985 | Kurita | 106/287.12 |
| 4,515,784 | 5/1985 | Bogardus et al. | 514/63 |
| 4,523,010 | 6/1985 | Lukach et al. | 536/91 |
| 4,529,523 | 7/1985 | Landoll | 252/8.55 D |
| 4,529,586 | 7/1985 | DeMarco et al. | 424/70 |
| 4,557,928 | 12/1985 | Glover | 424/70 |
| 4,559,227 | 12/1985 | Chandra et al. | 424/70 |
| 4,581,230 | 4/1986 | Grollier et al. | 424/74 |
| 4,584,189 | 4/1986 | Leipold | 424/54 |
| 4,610,874 | 9/1986 | Matravers | 424/70 |
| 4,683,004 | 7/1987 | Goddard | 106/170 |
| 4,684,704 | 8/1987 | Craig | 526/200 |
| 4,704,272 | 11/1987 | Oh et al. | 424/70 |
| 4,707,189 | 11/1987 | Nickol | 106/176 |
| 4,725,433 | 2/1988 | Matravers | 424/70 |
| 4,726,944 | 2/1988 | Osipow et al. | 424/70 |
| 4,728,457 | 3/1988 | Fieler et al. | 252/174.15 |
| 4,741,855 | 5/1988 | Grote et al. | 252/142 |
| 4,764,363 | 8/1988 | Bolich, Jr. | 424/47 |
| 4,788,006 | 11/1988 | Bolich, Jr. et al. | 252/550 |
| 4,834,968 | 5/1989 | Bolich, Jr. | 424/70 |
| 4,842,850 | 6/1989 | Vu | 424/70 |
| 4,902,499 | 2/1990 | Bolich, Jr. | 424/70 |
| 4,906,459 | 3/1990 | Cobb et al. | 424/70 |

FOREIGN PATENT DOCUMENTS

| | | |
|---|---|---|
| 155806 | 9/1985 | European Pat. Off. |
| 0170927 | 2/1986 | European Pat. Off. |
| 54-043210 | 4/1979 | Japan |
| 56-022716 | 3/1981 | Japan |
| 56-129300 | 10/1981 | Japan |
| 57-162768 | 10/1982 | Japan |
| 58-177909 | 10/1983 | Japan |
| 84007758 | 2/1984 | Japan |
| 85023151 | 6/1985 | Japan |
| 85026401 | 6/1985 | Japan |

(List continued on next page.)

OTHER PUBLICATIONS

Symposium notes, Division of Polymeric Materials:-Science and Engineering, 194th Nat'l Mtg of the ACS, New Orleans, Louisiana, Aug. 30–Sep. 4, 1987.

(List continued on next page.)

*Primary Examiner*—Thurman K. Page
*Assistant Examiner*—Susan S. Rucker
*Attorney, Agent, or Firm*—Leonard W. Lewis; Steven J. Goldstein

[57] ABSTRACT

Disclosed are hair conditioning compositions which provide cleaner hair conditioning than is experienced with traditional hair conditioners based on quaternary ammonium compounds and lipid materials. The present conditioning compositions are based on a substantially non-depositing vehicle base which comprises a primary thickening agent which is a nonionic long chain alkylated cellulose ether, a secondary thickening agent which is a water-insoluble surfactant, and a compatible solvent. These compositions comprise a mixture of conditioning agents including silicone conditioning agents, cationic surfactant conditioning agents, and high levels of fatty alcohol conditioning agents. These conditioning compositions provide optimized hair conditioning without the drawbacks associated with traditional hair conditioners, that is, dirty hair feel and quick resoiling of hair.

29 Claims, No Drawings

FOREIGN PATENT DOCUMENTS

| | | |
|---|---|---|
| 61-044972 | 3/1986 | Japan . |
| 61-053211 | 3/1986 | Japan . |
| 86023764 | 6/1986 | Japan . |
| 61-151105 | 7/1986 | Japan . |
| 61-158914 | 7/1986 | Japan . |
| 61-161214 | 7/1986 | Japan . |
| 61-186306 | 8/1986 | Japan . |
| 61-195138 | 8/1986 | Japan . |
| 62-294606 | 12/1987 | Japan . |
| 1532585 | 11/1978 | United Kingdom . |
| 2170216A | 7/1986 | United Kingdom . |
| 2185269A | 7/1987 | United Kingdom . |

OTHER PUBLICATIONS

Glass, J. Edward, ed., Advances in Chemistry Series, 0065-2393; 223, pp. 344-364.

Gelman, R. A., International Dissolving Pulp Conference, TAPPI, Feb. 1987, pp. 159-165.

Steiner, C. A., Polymer Prepr. (Am. Chem. Soc., Div. Polym. Chem.) 1985, 26(1), pp. 224-225.

Chem Abs. 103:27060b, Hercules Inc. Research Disclosure-252002, 1985 Publication.

Hercules Inc. Research Disclosure-252021.

Hercules Inc. Development Data-16 Publication.

Hercules Inc. Development Data-32 Publication.

Hercules Inc. Research Publication dated Nov. 2, 1984, entitled "Update WSP D-340 Performance in Surfactant Systems".

Chemical Abstracts, vol. 94, No. 2, May 1981, p. 373, column 1, Abstract No. 162601q.

Chemical Abstracts, vol. 97, No. 23, Dec. 1982, p. 324, column 1, Abstract No. 203098p.

Ser. No. 390,328, Bolich et al., filed Aug. 7, 1989 (Ser. No. 551,118—CIP application—filed Jul. 16, 1990).

Ser. No. 390,268, Bolich et al., filed Aug. 7, 1989 (Ser. No. 551,119—CIP application—filed Jul. 16, 1990).

Ser. No. 390,330, Bolich et al., filed Aug. 7, 1989 (Ser. No. 517,289—CIP application—filed May 1, 1990 and Ser. No. 551,120—2nd CIP Application filed Jul. 16, 1990).

CLEAN CONDITIONING COMPOSITIONS FOR HAIR

TECHNICAL FIELD

The present invention relates to unique hair conditioning compositions comprising silicone conditioning agents, cationic surfactant conditioning agents, and fatty alcohol conditioning agents, in a vehicle base which optimizes delivery of conditioning benefits while leaving hair feeling cleaner and remaining cleaner longer than traditional hair conditioner compositions.

BACKGROUND OF THE INVENTION

Typical hair conditioning products have a particular thick, creamy rheology that is desirable for such products. These products are based on the combination of a surfactant, which is generally a quaternary ammonium compound, and a fatty alcohol. This combination results in a gel-network structure which provides the composition with a thick, creamy rheology. However, while these same components deliver conditioning benefits to the hair, they also tend to deposit on hair in such a way that leaves hair looking and feeling dirty. Hair treated with such compositions tends to resoil much more quickly than untreated hair.

Alternative conditioning and thickening systems have been used in hair care compositions, but none have been found to date which provide this same desirable rheology, while at the same time providing superior conditioning benefits.

Though hair care products thickened with polymer thickeners can be made to have a thick rheology, these products generally are characterized by an undesirable "slimy" feel and do not hold their poured shape.

Nonionic water-soluble cellulose ethers are employed in a variety of applications, including hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Better thickening efficiency is realized with higher molecular weight cellulose ethers. However, production of such materials is difficult and expensive. Though crosslinking of these polymers is an alternative way to achieve high viscosity solutions, good crosslinking techniques are not known. Of course, high concentrations of polymers will also provide high viscosity but such an approach is inefficient and impractical, particularly due to the high expense involved. Furthermore, use of highly crosslinked polymers or high levels of polymeric thickeners may result in a vehicle system that is too elastic for the present uses.

A number of references teach the use of nonionic cellulose ethers and water-soluble gums for thickening hair care compositions. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum. Japanese Patent Publication 61-053211, published Mar. 7, 1986, discloses a hair colorant containing an aromatic alcohol, xanthan gum, and hydroxyethylcellulose.

Certain cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

These modified cellulose ethers have been disclosed for use in a variety of composition types. Landoll ('277) teaches the use of these materials in shampoo formulations. Hercules trade literature teaches the use of these materials in shampoos, liquid soaps, and lotions. U.S. Pat. No. 4,683,004, Goddard, issued July 28, 1987, discloses the use of these materials in mousse compositions for the hair. U.S. Pat. No. 4,485,089, Leipold, issued Nov. 27, 1984, teaches dentifrice compositions containing these materials.

These materials have been found to provide a rheology very much like the desirable gel-network structure of typical hair conditioners (without the slimy feel associated with most polymeric thickeners), when they are combined with water-insoluble surfactants at certain critical levels.

Silicone materials have been used to provide hair conditioning as an alternative to, or in combination with other hair conditioning materials. Siloxanes (see, for example, U.S. Pat. No. 3,208,911, Oppliger, issued Sept. 28, 1965) and siloxane-containing polymers have been taught for use in hair conditioning compositions. U.S. Pat. No. 4,601,902, Fridd et al., issued July 22, 1986, describes hair conditioning or shampoo/conditioner compositions which include a polydiorganosiloxane having quaternary ammonium substituted groups attached to the silicone, and a polydiorganosiloxane having silicon bonded substituents which are amino-substituted hydrocarbon groups. U.S. Pat. No. 4,654,161, Kollmeier et al., issued Mar. 31, 1987, describes a group of organopolysiloxane containing betaine substituents. When used in hair care compositions these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56-129,300, Lion Corporation, published Oct. 9, 1981, relates to shampoo/conditioner compositions which include an organopolysiloxane oxyalkylene copolymer together with an acrylic resin. U.S. Pat. No. 4,479,893, Hirota et al., issued Oct. 30, 1984, describes shampoo/conditioner compositions containing a phosphate ester surfactant and a silicon derivative (e.g., polyether- or alcohol-modified siloxanes). Polyether-modified polysiloxanes are also disclosed for use in shampoos in U.S. Pat. No. 3,957,970, Korkis, issued May 18, 1976. U.S. Pat. No. 4,185,087, Morlino, issued Jan. 22, 1980, describes quaternary derivatives of trialkylamino hydroxy organosilicon compounds which are said to have superior hair conditioning properties. U.S. Pat. No. 4,902,499, Bolich et al., issued Feb. 20, 1990, discloses hair care compositions comprising rigid silicone polymers, which are said to give both style retention and conditioning benefits. U.S. Pat. No. 4,906,459, Cobb et al., issued Mar. 6, 1990, discloses hair care compositions comprising a filler reinforced silicone gum, a silicone resin and a volatile carrier, which are said to provide both style retention and conditioning benefits.

Siloxane-derived materials have also been used in hair styling compositions. Japanese Published Application 56-092,811, Lion Corporation, published Dec. 27, 1979, describes hair setting compositions which comprise an amphoteric acrylic resin, a polyoxyalkylene-denatured organopolysiloxane, and polyethylene glycol. U.S. Pat. No. 4,744,978, Homan et al., issued May 17, 1988, describes hair setting compositions (such as hair sprays) which include the combination of a carboxy-functional polydimethylsiloxane and a cationic organic polymer containing amine or ammonium groups. Hair styling compositions which include polydiorganosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16, 1988. European Patent Application 117,360, Cantrell et al., published Sept. 5, 1984, discloses compositions, containing a siloxane polymer having at least one nitrogen-hydrogen bond, a surfactant, and a solubilized titanate, zirconate, or germanate, which act as both a conditioner and a hair styling aid.

Finally, European Patent Publication 155,806, Pings et al., published Sept. 25, 1985, discloses hair conditioning compositions comprising a silicone conditioning agent, a dimethicone copolyol, a cationic surfactant, and a lipid material. Such compositions are said to provide cleaner conditioning.

It has now been found that utilization of the vehicle bases of the present conditioner compositions enables the deposition of large amounts of conditioning agents including silicone conditioning agents, cationic surfactants, and, surprisingly, fatty alcohols, onto hair without the drawbacks generally associated with the use of such materials.

Hence, it is an object of the present invention to provide a hair conditioning composition characterized by a gel-network-like rheology, which provides superior hair conditioning without the drawbacks associated with typical hair conditioners.

It is also an object of the present invention to provide a hair conditioning composition which exhibits good deposition of hair conditioning agents, both in terms of quantity and quality, while minimizing deposition of the vehicle system components.

These and other objects will become readily apparent from the detailed description which follows.

SUMMARY OF THE INVENTION

The present invention relates to conditioning compositions for cleaner hair conditioning comprising:
 (a) from about 80% to about 98.9% of a vehicle base which comprises:
  (A) from about 0.1% to about 10.0%, by weight of the hair conditioning composition, of a nonionic cellulose ether having a sufficient degree of nonionic substitution, selected from the group consisting of methyl, hydroxyethyl, and hydroxypropyl to cause it to be water-soluble and being further substituted with a long chain alkyl radical having 10 to 22 carbon atoms in an amount between about 0.2 weight percent and the amount which renders said cellulose ether less than 1% by weight soluble in water;
  (B) from about 0.02% to about 10.0%, by weight of the hair conditioning composition, of a water-insoluble surfactant, having a molecular weight less than about 20,000; and
  (C) from about 65% to about 98.8%, by weight of the hair conditioning composition, of a compatible solvent; and
 (b) from about 1.1% to about 20% of a hair conditioning agent comprising;
  (A) from about 0.1% to about 18%, by weight of the hair conditioning composition, of a silicone conditioning agent; and
  (B) from greater than 1% to about 2%, by weight of the hair conditioning composition, of a fatty alcohol;
wherein said hair conditioning composition comprises no more than about 1.0% of water-soluble surfactants.

Preferably, up to about 2.5% of the conditioning composition comprises a quaternary ammonium compound water-insoluble surfactant.

DETAILED DESCRIPTION OF THE INVENTION

The essential as well as optional components of the present compositions are described below.

Clean Vehicle Base

The conditioning compositions of the present invention comprise a clean vehicle base, i.e., a substantially non-depositing vehicle base, which allows for optimized deposition of hair conditioning agents without the dirty hair feel resulting from the use of traditional hair conditioners. The vehicle base contains, as a first essential component, a primary thickening material. The primary thickener material is a hydrophobically modified nonionic water-soluble polymer. By "hydrophobically modified nonionic water-soluble polymer" is meant a nonionic water-soluble polymer which has been modified by the substitution with a sufficient amount of hydrophobic groups to make the polymer less soluble in water. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic to hydrophobic portion of the polymer is from about 10:1 to about 1000:1.

A number of existing patents disclose nonionic polymer materials which meet the above requirements and which are useful in the present invention. U.S. Pat. No. 4,496,708, Dehm et al., issued Jan. 29, 1985, teaches water-soluble polyurethanes having hydrophilic polyether backbones and pendant monovalent hydrophobic groups to result in a hydrophilic/lipophilic balance of between about 14 and about 19.5. U.S. Pat. No. 4,426,485, Hoy et al., issued Jan. 17, 1984, discloses a water-soluble thermoplastic organic polymer having segments of bunched monovalent hydrophobic groups. U.S. Pat. No. 4,415,701, Bauer, issued Nov. 15, 1983, discloses copolymers containing a monoepoxide and a dioxolane.

The most preferred primary thickeners for use in the present invention are disclosed in U.S. Pat. No. 4,228,277, Landoll, issued Oct. 14, 1980, which is incorporated herein by reference. The materials disclosed therein are thickeners comprising a nonionic long chain alkylated cellulose ether.

The cellulose ethers have a sufficient degree of nonionic substitution selected from the group consisting of methyl, hydroxyethyl and hydroxypropyl to cause them to be water-soluble. The cellulose ethers are further substituted with a hydrocarbon radical having about 10 to 22 carbon atoms in an amount between about 0.2 weight percent and the amount which renders said cellulose ether less than 1%, by weight, soluble in water. The cellulose ether to be modified is preferably one of low to medium molecular weight, i.e., less than about 800,000 and preferably between about 20,000 and 700,000 (about 75 to 2500 D.P.).

The Landoll patent teaches that any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropyl methyl→methyl.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

Methods for making these modified cellulose ethers are taught in Landoll ('277) at column 2, lines 36–65.

These materials have been found to be particularly desirable for use in the vehicle base of the conditioner compositions of the present invention. The materials are able to stabilize suspensions of dispersed conditioning agents, and when used with the water-insoluble surfactant secondary thickening agents and solvents of the present vehicle base, as described supra they produce rheologically thick products which lack the slimy feel characteristic of most polymeric thickeners.

One commercially available material which meets these requirements is NATROSOL PLUS Grade 330, a hydrophobically modified hydroxyethylcellulose available from Aqualon Company, Wilmington, Del. This material has a $C_{16}$ alkyl substitution of from about 0.5% to about 0.9% by weight. The hydroxyethyl molar substitution for this material is from about 2.8 to about 3.2. The average molecular weight for the water-soluble cellulose prior to modification is approximately 300,000.

An alternative material of this type for use in the present compositions is sold under the trade name NATROSOL PLUS CS Grade D-67, by Aqualon Company, Wilmington, Del. This material has a $C_{16}$ alkyl substitution of from about 0.30% to about 0.95%, by weight. The hydroxyethyl molar substitution for this material is from about 2.3 to about 3.3, and may be as high as about 3.7. The average molecular weight for the water soluble cellulose prior to modification is approximately 700,000.

The primary thickener component is present in the conditioner compositions of the present invention at from about 0.1% to about 10.0%, preferably from about 0.2% to about 5.0%, most preferably from about 0.6% to about 2.0%, by weight of the conditioner composition.

The vehicle base of the present conditioner compositions comprises, as a second essential component, a secondary thickening agent which is a water-insoluble surfactant material, having a molecular weight of less than about 20,000. By "water-insoluble surfactant" is meant surfactant materials which do not form clear isotropic solutions when dissolved in water at greater than 0.2 weight percent at ambient conditions. The water-insoluble surfactant material modifies the rheology of the vehicle base to make it more like the traditional conditioner gel-network rheology.

Nonlimiting examples of water-insoluble surfactants which can be used in the vehicle base of the conditioner compositions of the present invention can be selected from water-insoluble anionic, nonionic, cationic, zwitterionic and amphoteric surfactants.

Synthetic anionic surfactants include alkyl and alkyl ether sulfates. These materials have the respective formulae $ROSO_3M$ and $RO(C_2H_4O)_xSO_3M$, wherein R is alkyl or alkenyl of from about 10 to about 20 carbon atoms, x is 1 to 10, and M is a cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 14 to about 20 carbon atoms in both the alkyl and alkyl ether sulfates. The alcohols can be derived from fats, e.g., coconut oil or tallow, or can be synthetic. Stearyl alcohol and straight chain alcohols derived from tallow oil are preferred herein. Such alcohols are reacted with about 1 to about 10, and especially about 3, molar proportions of ethylene oxide and the resulting mixture of molecular species, having, for example, an average of 3 moles of ethylene oxide per mole of alcohol, is sulfated and neutralized.

Specific examples of alkyl ether sulfates which can be used in the present invention are sodium tallow alkyl diethylene glycol ether sulfate; and sodium tallow alkyl sulfate.

Another suitable class of anionic surfactants are the salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 18 to about 22, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which can be used in the present invention are the reaction products of fatty acids esterified with isethionic acid and neutralized with sodium hydroxide where, for example, the fatty acids are derived from tallow oil; sodium or potassium salts of fatty acid amides of methyl tauride in which the fatty acids, for example, are derived from tallow oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 24 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued July 25, 1967, incorporated herein by reference.

Another class of anionic organic surfactants are the β-alkyloxy alkane sulfonates. These compounds have the following formula:

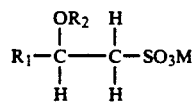

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers,* 1984 *Annual,* published by Allured Publishing Corporation, which is incorporated herein by reference. Also, U.S. Pat. No. 3,929,678, Laughlin et al., issued Dec. 30, 1975, discloses many other anionic as well as other surfactant types and is incorporated herein by reference.

Nonionic surfactants can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 2 to about 6 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 10% to about 40% polyoxyethylene by weight and having a molecular weight of from about 500 to about 4,000 resulting from the reaction of ethylene oxide groups with a hydrophobic base constituted of the reaction product of ethylene diamine and excess propylene oxide, said base having a molecular weight of the order of about 2,500 to about 10,000, are satisfactory.

3. The condensation product of aliphatic alcohols having from about 8 to about 20 carbon atoms, in either straight chain or branched chain configuration, with ethylene oxide, e.g., a tallow alcohol ethylene oxide condensate having from about 2 to about 10 moles of ethylene oxide per mole of tallow alcohol, the tallow alcohol fraction having from about 16 to about 18 carbon atoms.

4. Long chain tertiary amine oxides corresponding to the following general formula:

$$R_1R_2R_3N\rightarrow O$$

wherein R₁ contains an alkyl, alkenyl or monohydroxy alkyl radical of from about 12 to about 22 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyloctadecylamine oxide, oleyl-di(methyl) amine oxide, dimethylhexadecylamine oxide, behenyldimethylamine oxide.

5. Long chain tertiary phosphine oxides corresponding to the following general formula:

$$RR'R''P{\rightarrow}O$$

wherein R contains an alkyl, alkenyl or monohydroxyalkyl radical ranging from about 12 to about 22 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms. The arrow in the formula is a conventional representation of a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 12 to about 20 carbon atoms, from 0 to about 10 ethylene oxide moieties and from 0 to about 1 glyceryl moiety.

7. Silicone copolyols which may be polyalkylene oxide modified polydimethylsiloxanes of the following formulae:

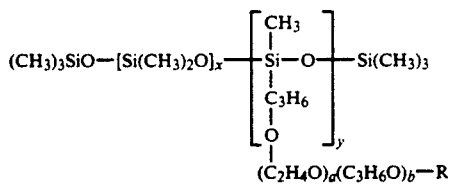

and

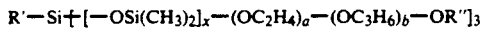

wherein R is hydrogen, an alkyl group having from 1 to about 12 carbon atoms, an alkoxy group having from 1 to about 6 carbon atoms or a hydroxyl group; R' and R'' are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein: U.S. Pat. No. 4,122,029, Gee, et al., issued Oct. 24, 1978; U.S. Pat. No. 4,265,878, Keil, issued May 5, 1981; and U.S. Pat. No. 4,421,769, Dixon, et al., issued Dec. 20, 1983. Such dimethicone copolyol materials are also disclosed, in hair compositions, in British Patent Application 2,066,659, Abe, published July 15, 1981 (incorporated by reference herein) and Canadian Patent 727,588, Kuehns, issued Feb. 8, 1966 (incorporated by reference herein). Commercially available dimethicone copolyols which can be used herein, include Silwet Surface Active Copolymers (manufactured by the Union Carbide Corporation); and Dow Corning Silicone Surfactants (manufactured by the Dow Corning Corporation).

8. Amide surfactants which include the ammonia, monoethanol, diethanol, and other alkanol amides of fatty acids having an acyl moiety of from about 8 to about 22 carbon atoms and represented by the general formula:

$$R_1-CO-N(H)_{m-1}(R_2OH)_{3-m}$$

wherein R is a saturated or unsaturated, aliphatic hydrocarbon radical having from 7 to 21, preferably from 11 to 17 carbon atoms; $R_2$ represents a $C_{1-4}$ alkalene group; and m is 1, 2 or 3, preferably 1. Specific examples of said amides are mono-ethanol coconut fatty acids amide and diethanol dodecyl fatty acid amide. These acyl moieties may be derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process. The monoethanol amides and diethanolamides of $C_{18-22}$ fatty acids are preferred.

Cationic surfactants useful in vehicle systems of the compositions of the present invention, contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., *McCutcheon's, Detergents & Emulsifiers*, (North American Edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued June 7, 1983.

Examples of such materials are quaternary ammonium-containing cationic surfactant materials. Among those useful herein are water-insoluble surfactants of the general formula:

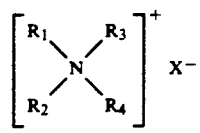

wherein R₁-R₄ can independently be selected from an aliphatic group of from about 1 to about 22 carbon atoms, C₁-C₃ alkyl, hydroxyalkyl, polyalkoxy or an aromatic, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

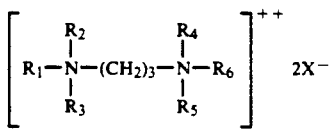

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and behenyl trimethyl ammonium chloride are preferred quaternary ammonium salts useful herein. Di-(hydrogenated tallow) dimethyl ammonium chloride is a particularly preferred quaternary ammonium salt for use in the present invention.

Salts of primary, secondary and tertiary fatty amines are also preferred cationic surfactant materials for use herein. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tridecyl amine, ethyl stearylamine, ethoxylated (2 moles E.O.) stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued June 23, 1981, incorporated by reference herein.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

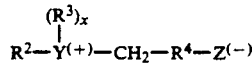

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as stearyl dimethyl carboxymethyl betaine, behenyl dimethyl carboxymethyl betaine, stearyl bis-(2-hydroxypropyl) carboxymethyl betaine, oleyl dimethyl gamma-carboxypropyl betaine. The sulfobetaines may be represented by behenyl dimethyl sulfopropyl betaine, stearyl dimethyl sulfopropyl betaine, and the like; hydrogenated tallow dimethyl betaine; amidobetaines and amidosulfobetaines, wherein the $RCONH(CH_2)_3$ radical is attached to the nitrogen atom of the betaine are also useful in this invention.

Examples of amphoteric surfactants which can be used in the vehicle systems of the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

Examples of preferred water-insoluble surfactants for use in the present invention are stearamide DEA, cocamide MEA, dimethyl stearamine oxide, glyceryl monooleate, sucrose stearate, PEG-2 stearamine, Ceteth-2, a polyethylene glycol ether of cetyl alcohol of the formula $CH_3-(CH_2)_{14}-CH_2-(OCH_2CH_2)_n-OH$, where n has an average value of 2 (commercially available under the trade name Brij 56 from ICI Americas), glycerol stearate citrate, dihydrogenated tallow dimethyl ammonium chloride, Poloxamer 181, a polyoxyethylene, polyoxypropylene block polymer of the formula

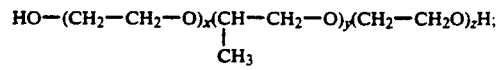

wherein on average x=3, y=30 and z=3 (commercially available from BASF Wyandotte under the trade name Pluronic L-61), hydrogenated tallow dimethyl betaine, and hydrogenated tallow amide DEA.

The water-insoluble surfactant secondary thickening agent is used with the primary thickener in the vehicle base of the conditioner compositions of the present invention at from about 0.02% to about 10.0%, preferably from about 0.05% to about 3.0%, most preferably from about 0.05% to about 2.0%, by weight of the composition.

A third essential component comprising the vehicle base of the conditioner compositions of the present invention is a solvent which is compatible with the other components in the present compositions. Generally, the solvent will comprise water or a water-lower alkanol mixture. The solvent is present in the compositions of the present invention at a level of from about 65% to about 98.8%, preferably from about 75% to about 95%, by weight of the conditioner composition.

The other vehicle base components are dispersed or mixed in the solvent to provide the thick rheology to the conditioner compositions formulated therewith that mimics the gel-network rheology of typical hair conditioning compositions.

The vehicle base of the conditioner compositions of the present invention preferably also contains a material which provides additional rheological benefits to the conditioner compositions. These materials are chelating agents. In general, such materials include monodentate and multidentate agents. Specific examples of useful chelating agents include ethylenediaminetetraacetic acid (EDTA), and salts thereof, nitrilotriacetic acid (NTA) and salts thereof, hydroxyethyl ethylene diamine triacetic acid (HEEDTA) and salts thereof, diethylene triamine pentaacetic acid (DTPA) and salts thereof, diethanol glycine (DEG) and salts thereof, ethanoldiglycine (EDG) and salts thereof, citric acid and salts thereof, phosphoric acid and salts. The most preferred of these is EDTA. The chelating agents tend to make the vehicle base of the conditioner compositions of the present invention smoother and less gelatinous in consistency.

If a chelating agent is present as a rheological aid in the compositions of the present invention it is present at a level of from about 0.05% to about 1.0%, preferably from about 0.05% to about 0.3%, by weight of the conditioner composition.

The vehicle base comprises from about 80% to about 98.9%, preferably from about 80% to about 98%, of the present hair conditioning compositions.

Hair Conditioning Agents

The present conditioning compositions comprise, dispersed in the substantially non-depositing vehicle base, as described supra, certain hair conditioning agents. These agents are materials that impart some conditioning benefits to the hair. Such benefits include soft hair feel (wet and dry), ease of hair combing (wet and dry), hair detangling benefits (wet and dry), antistatic benefits, and hair managability benefits. The present compositions comprise two essential hair conditioning agents, namely, silicone conditioning agents and fatty alcohol conditioning agents. Preferred compositions include cationic surfactants as at least a portion of the water-insoluble surfactant component and these materials also provide conditioning benefits.

The present conditioning compositions will comprise from about 1.1% to about 20%, preferably from about 1.5% to about 18%, of such hair conditioning agents.

Silicone Conditioning Agent

The first essential hair conditioning agent of the present compositions is a silicone conditioning agent. Silicone materials are known for use in providing hair conditioning, as described supra. It is also known that these materials provide a different form of conditioning than typical cationic surfactant/lipid vehicle material-based hair conditioners. Such materials tend not to leave hair as dirty looking or feeling as typical hair conditioning agents.

The present compositions will comprise from about 0.1% to about 18%, preferably from about 0.5% to about 15%, of a silicone conditioning agent.

In the past, use of high levels of certain silicone conditioning agents have tended to overcondition the hair, i.e., high levels of these materials have left hair feeling too soft, limp and generally, unmanageable. It has now been found that if these silicone conditioning materials are delivered out of the vehicle base of the present conditioner compositions, much higher levels of silicone conditioning agents may be used than have previously been usable, without the overconditioning negatives.

Examples of volatile silicone hair conditioning materials suitable for use in the compositions of the present invention have a boiling point in the range of about 99° C. to about 260° C. and have a solubility in water of less than about 0.1%. These volatile silicones may be either a cyclic or a linear polydimethylsiloxane. The number of silicon atoms in the cyclic silicones is preferably from about 3 to about 7, more preferably 4 or 5.

The general formula for such silicones is

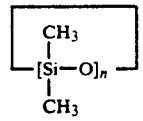

wherein n=3-7. The linear polydimethylsiloxanes have from about 3 to 9 silicon atoms and have the general formula:

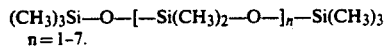

n=1-7.

Silicones of the above type, both cyclic and linear, are available from Dow Corning Corporation, Dow Corning 344, 345 and 200 fluids; Union Carbide, Silicone 7202 and Silicone 7158; and Stauffer Chemical, SWS-03314.

The linear volatile silicones generally have viscosities of less than about 5 centipoise at 25° C. while the cyclic materials have viscosities of less than about 10 centipoise. "Volatile" means that the material has a measurable vapor pressure. A description of volatile silicones is found in Todd and Byers, "Volatile Silicone Fluids for Cosmetics", *Cosmetics and Toiletries*, Vol. 91, January 1976, pp. 27-32, incorporated herein by reference.

The volatile silicone may be present in the conditioner compositions of this invention at a level of from about 1% to about 20%, preferably from about 2% to about 15%.

Nonvolatile silicone fluids are also useful as a silicone conditioning agent in the compositions of the present invention. Examples of such materials include polydimethylsiloxane gums, aminosilicones and phenylsilicones. More specifically, materials such as polyalkyl or polyaryl siloxanes with the following structure:

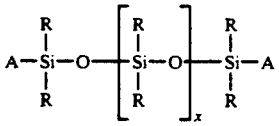

wherein R is alkyl or aryl, and x is an integer from about 7 to about 8,000, may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Suitable methods for preparing these silicone materials are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

Preferred silicone gums for use in the present invention are polydimethyl siloxane gums or polyphenyl methyl siloxane gums having viscosities greater than about 1,000,000 centipoise, which are present in the conditioner compositions at levels of from about 0.015% to about 9.0%, preferably from about 0.5% to about 2%.

Other useful silicone materials include materials of the formula:

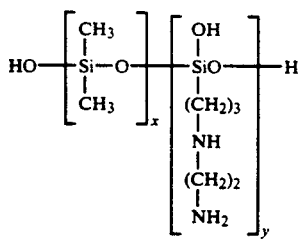

(I)

in which x and y are integers which depend on the molecular weight, the average molecular weight being approximately between 5,000 and 10,000. This polymer is also known as "amodimethicone".

Other silicone cationic polymers which can be used in the present compositions correspond to the formula:

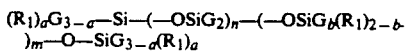

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

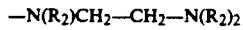

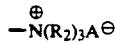

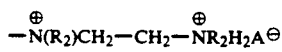

in which $R_2$ is chosen from the group consisting of hydrogen, phenyl, benzyl, a saturated hydrocarbon radical, preferably an alkyl radical containing from 1 to 20 carbon atoms, and $A^\ominus$ denotes a halide ion.

These compounds are described in greater detail in European Patent Application EP 95,238. An especially preferred polymer corresponding to this formula is the polymer known as "trimethylsilylamodimethicone" of formula:

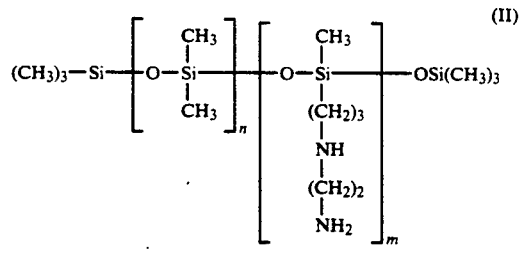

(II)

Other silicone cationic polymers which can be used in the present compositions correspond to the formula:

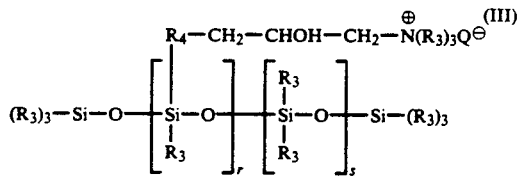

(III)

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_8$, alkyleneoxy radical;

$Q^\ominus$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Preferred silicone conditioning agents in the present compositions comprise combinations of volatile silicone fluids having viscosities of less than about 10 centipoise, and from about 0.015% to about 9.0%, preferably from about 0.5% to about 2.0%, of silicone gums having viscosities greater than about 1,000,000 centipoise, at ratios of volatile fluid to gum of from about 90:10 to about 10:90, preferably from about 85:15 to about 50:50.

Preferable nonvolatile silicone materials for use in the present invention comprise combinations of nonvolatile silicone fluids having viscosities of less than about 100,000 cP (centipoise), and from about 0.015% to about 9.0%, preferably from about 0.5% to about 2.0%, of silicone gums, having viscosities greater than about 1,000,000 cP, especially polydimethylsiloxane gums and polyphenylmethylsiloxane gums, at ratios of fluid to gum of from about 70:30 to about 30:70, preferably from about 60:40 to about 40:60.

Also preferred for use as an additional silicone conditioning agent in the present compositions is up to about 1.0% of a trimethylsilyl amodimethicone.

Alternative silicone conditioning agents for use in the conditioner compostions of the present invention are silicone polymer materials which provide both style retention and conditioning benefits to the hair. Although silicone fluids are useful in the present compositions, preferred silicone polymers are rigid silicone polymers.

Some examples of such materials include, but are not limited to, filler reinforced polydimethyl siloxane gums including those having end groups such as hydroxyl; cross linked siloxanes, such as organic substituted silicone elastomers; organic substituted siloxane gums, including those having end groups such as hydroxyl; resin reinforced siloxanes; and cross linked siloxane polymers.

The rigid silicone polymers useful in the present invention have complex viscosities of at least $2 \times 10^5$ poise (P), preferably about $1 \times 10^7$ poise, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

One such siloxane gum is a diphenyl-dimethyl polysiloxane gum having a molecular weight of at least about 500,000, and must be diphenyl substituted to the extent of 3% or more, preferably at least about 5%.

The siloxane gums may also be filler reinforced to provide additional rigidity. Silica is the preferred filler. Generally such reinforced gums comprise up to about 15-20% silica.

Silicone elastomers useful in the compositions of the present invention are the materials described in U.S. Pat. No. 4,221,688, Johnson et al., issued Sept. 9, 1980, incorporated herein by reference. The actual material described in the patent and what can be put into the present compositions is an aqueous emulsion which dries to form an elastomer upon removal of the water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to about 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of a diorganotindicarbonate (e.g., dioctyl tindilaurate) catalyst is from 0.1 to 2 parts. The elastomer emulsion is used in an amount of from about 0.1% to about 5%, preferably from about 0.5% to about 4%, of the total composition.

Silicone resins useful in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use.

Other rigid silicone polymers of use herein are those siloxanes which have been sparingly crosslinked but are still soluble in solvents such as cyclomethicone. Precursors for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

Generally, the silicone gum, if used in the present compositions, is dissolved in a volatile carrier, or mixtures thereof, prior to incorporation into the hair care compositions. Preferably, the volatile carrier is present in the hair care composition at from about 0.1% to about 20% of the hair care composition. These materials can comprise the volatile silicone fluids described supra.

If used in the present compositions, the rigid silicone polymer and carrier preferably comprises from about 0.1% to about 2.5% of a polydimethylsiloxane gum; from about 0.02% to about 0.7% of fumed silica, and from about 0.4% to about 18% of a volatile silicone carrier.

Cationic Surfactant Conditioning Agent

Cationic surfactant materials are commonly used in hair conditioning compositions to provide hair conditioning benefits. However, such materials have tended to leave the hair feeling coated and dirty. Such materials have also tended to make the hair resoil at a faster rate than untreated hair.

It has now been found that when these materials are delivered out of the vehicle base of the present conditioner compositions, these effects are lessened. Hence, the result is that these materials can be used to provide enhanced hair conditioning without the drawbacks of dirty hair feel.

The use of these cationic surfactant conditioning materials with the silicone conditioning agents of the present invention provide optimized conditioning benefits. The silicone conditioning agents provide soft hair feel benefits, as well as detangling and ease of combing. The cationic surfactants provide static control benefits, as well as other conditioning benefits.

The cationic surfactant conditioning agents useful in the present compositions are actually a subclass of the water-insoluble surfactant materials of the present invention. When they are included, they comprise at least a portion of the water-insoluble surfactant component. In addition to providing the vehicle benefits, these materials also provide conditioning benefits. Up to about 2.5%, preferably from about 0.5% to about 2.0%, of the conditioner composition comprises a quaternary ammonium compound water-insoluble surfactant material.

The preferred of these materials are of the following classes. The first is quaternary ammonium-containing cationic surfactant materials. Among those useful herein are materials of the general formula:

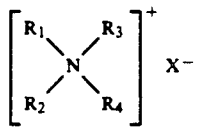

wherein $R_1$-$R_4$ can independently be selected from an aliphatic group of from about 1 to about 22 carbon atoms, $C_1$-$C_3$ alkyl, hydroxyalkyl, polyalkoxy or an aromatic, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

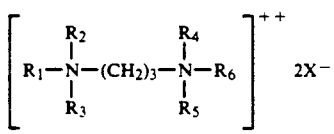

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present compositions include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and behenyl trimethyl ammonium chloride are preferred quaternary ammonium salts useful herein. Di-(hydrogenated tallow) dimethyl ammonium chloride is a particularly preferred water-insoluble quaternary ammonium salt for use as a conditioning agent in the present compositions.

Salts of primary, secondary and tertiary fatty amines are also preferred water-insoluble cationic surfactant materials for use herein as hair conditioning agents. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tridecyl amine, ethyl stearylamine, ethoxylated (2 moles E.O.) stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present compositions are disclosed in U.S. Pat. No. 4,275,055, Nachtigal, et al., issued June 23, 1981, incorporated by reference herein. The preferred of these amines for use as a conditioning agent herein is stearamido propyldimethyl amine. A commercially available material is sold under the trade name Lexamine ® by Inolex, Company. Preferably, up to 1% of the conditioning composition comprises a stearamido propyldimethyl amine water-insoluble surfactant, as a hair conditioning agent.

Fatty Alcohol Conditioning Agent

Fatty alcohols are commonly used in hair conditioning compositions to condition hair. However, like cationic surfactants, such materials have tended to leave the hair feeling coated and dirty. Such materials also have tended to make the hair resoil at a faster rate than hair that has not been treated with such materials. This is especially true as the level of this component in the hair conditioning composition is increased. It is important to remember that small differences in the level of fatty alcohol will have a big impact of hair feel. Even levels as low as 1-2% of fatty alcohol in traditional conditioning products, will result in these negative hair feel drawbacks.

Fatty alcohol materials are desirably included in hair conditioner compositions, however, to provide hair managability benefits to the user. Such materials enable ease of hair styling.

It has now surprisingly been found that when fatty alcohol materials are delivered out of the present vehicle base of the conditioner compositions of the present invention, these negative conditioning effects are lessened. Hence, the result is that these materials can be used at higher levels than previously thought to provide enhanced hair conditioning without the usual drawbacks of coated, dirty hair feel.

The use of these conditioning materials with the silicone conditioning agents and cationic surfactant conditioning agents of the present invention provide optimized conditioning benefits. The silicone conditioning agents provide soft hair feel benefits, as well as ease of combing; the cationic surfactants provide anti-static benefits; and the fatty alcohol materials provide increased managability benefits. The result is optimized conditioning in all respects.

Fatty alcohol materials that are useful as conditioning agents herein are described in *Bailey's Industrial Oil and Fat Products*, (3rd edition, D. Swern, ed. 1979) incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe et al., issued Aug. 21, 1979; U.S. Pat. No. 4,269,824, Villamarin et al., issued May 26, 1981; and British Specification 1,532,585, published Nov. 15, 1978.

Specific examples of fatty alcohol materials included among those that may be used herein include stearyl-, cetyl-, myristyl-, behenyl-, lauryl-, oleyl alcohols and mixtures thereof. Especially preferred fatty alcohols for use herein are cetyl alcohol and stearyl alcohol containing from about 55% to about 65% (by weight of the mixture) of cetyl alcohol.

For the reasons described above, it has now surprisingly been found that fatty alcohols can be delivered out of the present compositions at levels higher than was previously thought without the usual dirty hair feel drawbacks associated with such materials. Hence, the present compositions may comprise from greater than 1% to about 2%, preferably from greater than 1% to about 1.5%, of fatty alcohol materials. The use of such compositions on hair will leave hair feeling and looking cleaner and less coated than traditional fatty alcohol-based conditioner compositions.

Additional Hair Conditioning Agents

Other hair conditioning agents which can be used in the present compositions to provide enhanced conditioning benefits are hydrolyzed animal protein conditioning agents. An example of a commercially available material is sold under the tradename Crotein Q ® from Croda, Inc.

Such materials are present in the conditioner compositions at levels of from about 0.1% to about 1.5%.

Optional Components

The compositions of the present composition may also comprise a number of optional components to provide cosmetic or aesthetic benefits. Examples of such materials include coloring agents, such as any of the FD&C or D&C dyes; opacifiers; pearlescent aids, such as ethylene glycol distearate or $TiO_2$ coated mica; pH modifiers, such as citric acid, succinic acid, phosphoric acid, sodium hydroxide, and sodium carbinate; preservatives, such as benzyl alcohol, ethyl paraben, propyl paraben, and imidazolidonyl urea; emulsifiers such as Ceteareth-20 and glyceryl monostearate; and antioxidants. Such agents are generally used individually at a level of from about 0.001% to about 10%, preferably from about 0.01% to about 5%, of the conditioner composition.

The present hair conditioner compositions must be substantially free of water-soluble surfactants. High levels of these materials are not compatible with the vehicle base of the present conditioner compositions. By "substantially free of water-soluble surfactants" is meant that the compositions comprise less than an amount of such surfactants that will destroy the unique desirable rheology that is characteristic of the present compositions. Generally, this will mean that the present compositions comprise no more than about 1%, preferably no more than about 0.5%, of such materials. Examples of specific water-soluble surfactants that will have this effect at levels higher than about 1%, include surfactants commonly used at high levels in shampoo compositions. These include alkyl sulfates and ethoxylated alkyl sulfates, such as ammonium lauryl sulfate; amphoteric surfactants which are derivatives of aliphatic secondary and tertiary amines; nonionic surfactants produced by the condensation of alkylene oxide groups with an organic hydrophilic compound, such as laureth-23 (sold under the trade name Brij 35 ® by ICI Americas); and high alkyl betaines, sulfo betaines, amido betaines, and amidosulfobetaines, such as cetyl betaine.

Methods of Manufacture

The compositions of the present invention may be manufactured using conventional formulation and mixing techniques. In one procedure for manufacture, the silicone conditioner, quaternary ammonium surfactant, and at least a portion of the solvent component are premixed prior to the addition of the remaining components. Methods of making compositions of the present invention are described more specifically in the following examples.

Method for Conditioning Hair

The present invention also provides methods for conditioning hair. The present compositions are used in conventional ways to provide the optimized hair conditioning benefits of the present invention. Such methods generally involve application of an effective amount of the conditioning composition to the hair, which is massaged through and then rinsed from the hair. By "effective amount" is meant an amount sufficient to provide the desired conditioning benefits considering the length, texture and condition of the hair.

After the hair is treated with the present conditioning compositions the hair is dried and styled in the usual ways of the user. The hair conditioning compositions provide optimized hair conditioning benefits, such as soft wet and dry hair feel, ease of wet and dry hair combing and hair detangling, increased hair managability, and anti-static benefits. At the same time, the hair is left looking and feeling cleaner than is experienced with traditional cationic surfactant/fatty alcohol-based hair conditioners.

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified.

EXAMPLE I

The following is a hair conditioning composition representative of the present invention.

| Component | Weight % |
| --- | --- |
| Polydimethylsiloxane Gum | 1.00 |
| Decamethylcyclopentasiloxane | 5.67 |
| Adogen 442 - 100P (quaternium-18) | 1.00 |
| Natrosol Plus Grade D-67[1] | 0.70 |
| Stearamide DEA | 0.44 |
| Stearyl Alcohol | 0.60 |
| Cetyl Alcohol | 0.90 |
| Disodium EDTA | 0.10 |

| Component | Weight % |
| --- | --- |
| Sodium Citrate | 0.04 |
| Citric Acid | 0.07 |
| Fragrance | 0.25 |
| Kathon (preservative) | 0.033 |
| DRO Water | q.s. to 100 |

[1] hydrophobically modified hydroxyethyl cellulose available from Aqualon Co.

The composition is prepared as follows. The Adogen 442 is first premixed with water and heated to about 77° C, with mixing until melted. The premix is then cooled to about 60° C., and the siloxane gum/cyclopentasiloxane mixture is added. The premix is mixed for an additional 10 minutes.

The remaining water, citric acid, sodium citrate, and EDTA are separately combined and heated with mixing to about 65° C. The cetyl alcohol, stearyl alcohol, and stearamide DEA are then added with mixing. The Natrosol Plus is then added with mixing until the composition thickens. The premix is then added with mixing and the composition is cooled to about 50° C. The perfume and Kathon are added and the composition is cooled with milling to ambient temperature.

The resulting hair conditioner provides superior hair conditioning as compared to traditional hair conditioners without the usual tradeoffs of dirty hair look and feel.

Other hair conditioning agents can also be present in the composition, for example, stearamidopropyl dimethyl amine at up to about 1%, trimethylsilylamodimethicone at up to about 0.75%, hydrolyzed animal protein at up to about 1%, and mixtures thereof.

EXAMPLE II

A hair conditioning composition representative of the present invention is as follows.

| Component | Weight % |
| --- | --- |
| Polydimethylsiloxane Gum | 2.00 |
| Decamethylcyclopentasiloxane | 11.33 |
| Adogen 442 - 100P (quaternium-18) | 2.00 |
| Natrosol Plus Grade D-67[1] | 0.70 |
| Stearamide DEA | 0.44 |
| Stearyl Alcohol | 0.70 |
| Cetyl Alcohol | 1.05 |
| Ceteareth-20 | 0.35 |
| Disodium EDTA | 0.10 |
| Sodium Citrate | 0.04 |
| Citric Acid | 0.07 |
| Fragrance | 0.25 |
| Kathon (preservative) | 0.033 |
| DRO Water | q.s. to 100 |

[1] hydrophobically modified hydroxyethyl cellulose available from Aqualon Co.

This composition is prepared as is described in Example I, except that the Ceteareth-20 is added with the cetyl and stearyl alcohols.

The resulting hair conditioner provides superior hair conditioning as compared to traditional hair conditioners without the usual tradeoffs of dirty hair look and feel.

What is claimed is:

1. A hair conditioning composition comprising:
   (a) from about 80% to about 98.9%, by weight of the hair conditioning composition, of a vehicle base which comprises:
      (A) from about 0.1% to about 10.0%, by weight of the hair conditioning composition, of a nonionic cellulose ether having a sufficient degree of nonionic substitution, selected from the group consisting of methyl, hydroxyethyl, and hydroxypropyl to cause it to be water-soluble and being further substituted with a long chain alkyl radical having 10 to 24 carbon atoms in an amount between about 0.2 weight percent and the amount which render said cellulose ether less than 1% by weight soluble in water;
      (B) from about 0.02% to about 10.0%, by weight of the hair conditioning composition, of a water-insoluble surfactant, having a molecular weight less than about 20,000; and
      (C) from about 65% to about 98.8%, by weight of the hair conditioning composition, of a compatible solvent; and
   (b) from about 1.1% to about 20%, by weight of the hair conditioning composition, of a hair conditioning agent comprising;
      (A) from about 0.1% to about 18%, by weight of the hair conditioning composition, of a silicone conditioning agent; and
      (B) from greater than 1% to about 2%, by weight of the hair conditioning composition, of a fatty alcohol;
   wherein said hair conditioning composition comprises no more than about 1.0% of water-soluble surfactants.

2. The composition of claim 1 wherein a quaternary ammonium compound comprises at least a portion of the water-insoluble surfactant, at a level up to about 2.5% by weight of the conditioning composition.

3. The composition of claim 2 wherein the nonionic cellulose ether comprises from about 0.2% to about 5.0% of the hair conditioning composition.

4. The composition of claim 3 wherein the nonionic cellulose ether comprises the long-chain alkyl radical attached via an ether linkage.

5. The composition of claim 4 wherein the nonionic cellulose ether comprises a water-soluble hydroxypropyl cellulose substituted with a long-chain alkyl radical having 10 to 22 carbon atoms in an amount between about 0.2 weight percent and the amount which renders the hydroxypropyl cellulose less than 1% by weight soluble in water.

6. The composition of claim 4 wherein the nonionic cellulose ether comprises a water-soluble hydroxyethyl cellulose substituted with a long-chain alkyl radical having 10 to 22 carbon atoms in an amount between about 0.2 weight percent and the amount which renders the hydroxyethyl cellulose less than 1% by weight soluble in water.

7. The composition of claim 6 wherein the hydroxyethyl cellulose prior to substitution with the long chain alkyl group has a molecular weight of about 50,000 to 700,000.

8. The composition of claim 7 wherein the water-soluble hydroxyethyl cellulose is substituted with a long chain alkyl radical having about 16 carbon atoms in an amount between about 0.30% to about 0.95%, by weight; the hydroxyethyl molar substitution is from about 2.3 to about 3.7; and the average molecular weight of the unsubstituted cellulose is from about 300,000 to about 700,000.

9. The composition of claim 2 wherein the water-insoluble surfactant is selected from the group consisting of stearamide DEA, cocamide MEA, dimethyl stearamine oxide, glyceryl monooleate, sucrose stearate, PEG-2 stearamine, Ceteth-2, glycerol stearate citrate, Poloxamer 181, hydrogenated tallow dimethyl betaine, hydrogenated tallow amide DEA, and mixtures thereof.

10. The composition of claim 9 wherein the water-insoluble surfactant comprises hydrogenated tallow amide DEA.

11. The composition of claim 2 wherein the quaternary ammonium compound hair conditioning agent comprises dihydrogenated tallow dimethyl ammonium chloride.

12. The composition of claim 2 wherein the fatty alcohol is selected from the group consisting of stearyl alcohol, cetyl alcohol, myristyl alcohol, behenyl alcohol, lauryl alcohol, oleyl alcohol and mixtures thereof.

13. The composition of claim 12 wherein the fatty alcohol is selected from the group consisting of cetyl alcohol, stearyl alcohol, and mixtures thereof.

14. The composition of claim 2 additionally comprising from about 0.05% to about 1.0% of a chelating agent which is selected from the group consisting of ethylene diamine tetracetic acid and salts thereof, nitrilo triacetic acid and salts thereof, hydroxyethylene diamine triacetic acid and salts thereof, diethylene triamine penta-acetic acid and salts thereof, diethanol glycine and salts thereof, ethanol diglycine and salts thereof, citric acid and salts thereof, phosphoric acid and salts thereof.

15. The composition of claim 2 wherein the silicone conditioning agent comprises from about 1% to about 20% of a volatile silicone fluid having a viscosity at 25° C. of less than about 10 centipoise.

16. The composition of claim 2 wherein the silicone conditioning agent comprises a non-volatile silicone fluid having a viscosity at 25° C. of less than about 100,000 centipoise.

17. The composition of claim 2 wherein the silicone conditioning agent comprises from about 0.015% to about 9.0% of a silicone gum having a viscosity at 25° C. greater than about 1,000,000 centipoise.

18. The composition of claim 17 wherein the silicone gum is selected from the group consisting of polydimethylsiloxane gums and polyphenylmethylsiloxane gums.

19. The composition of claim 2 wherein the silicone conditioning agent comprises a combination of a volatile silicone fluid having a viscosity at 25° C. of less than about 10 centipoise, and from about 0.015% to about 9.0% of a silicone gum having a viscosity at 25° C. of greater than about 1,000,000 centipoise, wherein the ratio of fluid to gum is from about 90:10 to about 10:90.

20. The composition of claim 2 wherein the silicone conditioning agent comprises a combination of a non-volatile silicone fluid having a at 25° C. viscosity of less than about 100,000 centipoise and from about 0.015% to about 9.0% of a silicone gum having a viscosity at 25° C. greater than about 1,000,000 centipoise; wherein the ratio of fluid to gum is from about 70:30 to about 30:70.

21. The composition of claim 2 which comprises up to about 1.0% of a trimethylsilyl- amodimethicone as at least a portion of the silicone conditioning agent.

22. The composition of claim 2 wherein a stearamidopropyldimethyl amine comprises at least a portion of the water-insoluble surfactant component at a level up to about 1% of the conditioning composition.

23. The composition of claim 2 which additionally comprises from about 0.1% to about 1.5% of a hydrolyzed animal protein hair conditioning agent.

24. A hair conditioning composition comprising:

(a) from about 80% to about 98%, by weight of the hair conditioning composition, of a vehicle base which comprises:
  (A) from about 0.2% to about 5.0%, by weight of the hair conditioning composition, of a nonionic cellulose ether substituted with a long chain alkyl radical having about 16 carbon atoms in an amount between about 0.30% to about 0.95%, by weight; a hydroxyethyl molar substitution of from about 2.3 to about 3.7; and an average molecular weight of unsubstituted cellulose of from about 300,000 to about 700,000;
  (B) from about 0.05% to about 0.3%, by weight of the hair conditioning composition, of hydrogenated tallow amide DEA;
  (C) from about 0.05% to about 0.3%, by weight of the hair conditioning composition of a chelating agent selected from the group consisting of ethylene diamine tetra acetic acid, and salts thereof; citric acid, and salts thereof; and mixtures thereof; and
  (D) from about 75% to about 95%, by weight of the hair conditioning composition, of water; and
(b) from about 1.5% to about 18%, by weight of the hair conditioning composition, of a hair conditioning agent comprising;
  (A) from about 0.5% to about 15%, by weight of the hair conditioning composition, of a combination of a volatile silicone fluid having a viscosity at 25° C. of less than about 10 centipoise, and from about 0.5% to about 2.0% of a silicone gum having a viscosity at 25° C. greater than about 1,000,000 centipoise; wherein the ratio of fluid to gum is from about 85:15 to about 50:50;
  (B) from about 0.5% to about 2.0%, by weight of the hair conditioning composition, of dihydrogenated tallow dimethyl ammonium chloride; and
  (C) from greater than 1% to about 1.5%, by weight of the hair conditioning composition, of a fatty alcohol selected from the group consisting of cetyl alcohol, stearyl alcohol, and mixtures thereof;

wherein said hair conditioning composition comprises no more than about 0.5% of water-soluble surfactants.

25. A hair conditioning composition comprising:
(a) from about 80% to about 98%, by weight of the hair conditioning composition, of a vehicle base which comprises:
  (A) from about 0.2% to about 5.0%, by weight of the hair conditioning composition, of a nonionic cellulose ether substituted with a long chain alkyl radical having about 16 carbon atoms in an amount between about 0.30% to about 0.95%, by weight; a hydroxyethyl molar substitution of from about 2.3 to about 3.7; and an average molecular weight of unsubstituted cellulose of from about 300,000 to about 700,000;
  (B) from about 0.05% to about 3.0%, by weight of the hair conditioning composition, of hydrogenated tallow amide DEA;
  (C) from about 0.05% to about 0.3%, by weight of the hair conditioning composition of a chelating agent selected from the group consisting of ethylene diamine tetra acetic acid, and salts thereof; citric acid, and salts thereof; and mixtures thereof; and (D) from about 75% to about 95%, by weight of the hair conditioning composition, of water; and (b) from about 1.5% to about 18%, by weight of the hair conditioning composition, of a hair conditioning agent comprising;

(A) from about 0.5% to about 15%, by weight of the hair conditioning composition, of a combination of a non-volatile silicone fluid having a viscosity at 25° C. of less than about 100,000 centipoise and from about 0.5% to about 2.0% of a silicone gum having a viscosity at 25° C. greater than about 1,000,000 centipoise; wherein the ratio of fluid to gum is from about 60:40 to about 40:60;

(B) from about 0.5% to about 2.0%, by weight of the hair conditioning composition, of dihydrogenated tallow dimethyl ammonium chloride; and (C) from greater than 1% to about 1.5%, by weight of the hair conditioning composition, of a fatty alcohol selected from the group consisting of cetyl alcohol, stearyl alcohol, and mixtures thereof;

wherein said hair conditioning composition comprises no more than about 0.5% of water-soluble surfactants.

26. A method for providing conditioning to hair, said method comprising treating the hair with the composition of claim 1.

27. A method for providing conditioning to hair, said method comprising treating the hair with the composition of claim 24.

28. A method for providing conditioning to hair, said method comprising treating the hair with the composition of claim 25.

29. A method of manufacturing a hair conditioning composition according to claim 1 wherein a quaternary ammonium compound comprises at least a portion of the water-insoluble surfactant, at a level up to about 2.5% by weight of the conditioning composition, comprising the step of premixing the silicone conditioning agent, the quaternary ammonium compound, and at least a portion of the solvent prior to mixing with the remaining components.

* * * * *